US006203993B1

(12) United States Patent
Shuber et al.

(10) Patent No.: US 6,203,993 B1
(45) Date of Patent: Mar. 20, 2001

(54) METHODS FOR THE DETECTION OF NUCLEIC ACIDS

(75) Inventors: Anthony P. Shuber, Milford, MA (US); Stanley N. Lapidus, Bedford, NH (US); George Q. Daley, Weston, MA (US)

(73) Assignees: Exact Science Corp., Maynard, MA (US); Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 09/542,103

(22) Filed: Apr. 4, 2000

Related U.S. Application Data

(63) Continuation of application No. 09/098,180, filed on Jun. 16, 1998, which is a continuation-in-part of application No. 08/876,857, filed on Jun. 16, 1997, now Pat. No. 5,928,870, which is a continuation-in-part of application No. 08/700,583, filed on Aug. 14, 1996, now Pat. No. 5,670,325.

(51) Int. Cl.[7] .................................................... C12Q 1/68
(52) U.S. Cl. ............................................. 435/6; 536/23.3
(58) Field of Search ................................. 435/6; 536/23.3

(56) References Cited

U.S. PATENT DOCUMENTS

| | | |
|---|---|---|
| 4,683,195 | 7/1987 | Mullis et al. . |
| 4,705,050 | 11/1987 | Markham . |
| 4,735,905 | 4/1988 | Parker . |
| 4,786,718 | 11/1988 | Weinberg et al. . |
| 4,857,300 | 8/1989 | Makksem . |
| 4,871,838 | 10/1989 | Bos et al. . |
| 4,981,783 | 1/1991 | Augenlicht . |
| 4,982,615 | 1/1991 | Sultan et al. . |
| 5,087,617 | 2/1992 | Smith . |
| 5,126,239 | 6/1992 | Livak et al. . |
| 5,137,806 | 8/1992 | LeMaistre et al. . |
| 5,149,506 | 9/1992 | Skiba et al. . |
| 5,196,167 | 3/1993 | Guadagno et al. . |
| 5,248,671 | 9/1993 | Smith . |
| 5,272,057 | 12/1993 | Smulson et al. . |
| 5,302,509 | 4/1994 | Cheeseman . |
| 5,330,892 | 7/1994 | Vogelstein et al. . |
| 5,331,973 | 7/1994 | Fiedler et al. . |
| 5,348,855 | 9/1994 | Dattagupta et al. . |
| 5,352,775 | 10/1994 | Albertsen et al. . |
| 5,362,623 | 11/1994 | Vogelstein et al. . |
| 5,369,004 | 11/1994 | Polymeropoulos et al. . |
| 5,378,602 | 1/1995 | Polymeropoulos et al. . |
| 4,101,279 | 7/1978 | Aslam . |
| 4,309,782 | 1/1982 | Paulin . |
| 4,333,734 | 6/1982 | Fleisher . |
| 4,445,235 | 5/1984 | Slover et al. . |
| 4,535,058 | 8/1985 | Weinberg et al. . |

(List continued on next page.)

FOREIGN PATENT DOCUMENTS

| | | |
|---|---|---|
| 11325/95 | 10/1994 | (AU) . |
| 0 284 362 A2 | 9/1988 | (EP) . |
| 0 337 498 | 10/1989 | (EP) . |
| 0 390 323 A2 | 10/1990 | (EP) . |
| 0 390 323 A3 | 10/1990 | (EP) . |
| 0 407 789 A1 | 1/1991 | (EP) . |
| 0 407 789 B1 | 1/1991 | (EP) . |
| 608 004 A2 | 7/1994 | (EP) . |
| 0 259 031 B1 | 11/1994 | (EP) . |
| 0 664 339 A1 | 7/1995 | (EP) . |
| 0 785 280 | 7/1997 | (EP) . |
| WO 92/13103 | 8/1992 | (WO) . |
| WO 93/18186 | 9/1993 | (WO) . |
| WO 93/20233 | 10/1993 | (WO) . |
| WO 93/24657 | 12/1993 | (WO) . |
| WO 94/00603 | 1/1994 | (WO) . |
| WO 94/09161 | 4/1994 | (WO) . |
| WO 94/10575 | 5/1994 | (WO) . |
| WO 94/11383 | 5/1994 | (WO) . |
| WO 95/07361 | 3/1995 | (WO) . |
| WO 95/09928 | 4/1995 | (WO) . |
| WO 95/09929 | 4/1995 | (WO) . |
| WO 95/12606 | 5/1995 | (WO) . |
| WO 95/13397 | 5/1995 | (WO) . |
| WO 95/15400 | 6/1995 | (WO) . |
| WP 95/16792 | 6/1995 | (WO) . |
| WO 95/18818 | 7/1995 | (WO) . |
| WO 95/19448 | 7/1995 | (WO) . |
| WO 95/25813 | 9/1995 | (WO) . |
| WO 95/31728 | 11/1995 | (WO) . |
| WO 96/01907 | 1/1996 | (WO) . |
| WO 96/06951 | 3/1996 | (WO) . |
| WO 96/08514 | 3/1996 | (WO) . |
| WO 96/12821 | 5/1996 | (WO) . |
| WO 96/13611 | 5/1996 | (WO) . |
| WO 97/23651 | 3/1997 | (WO) . |
| WO 97/38135 | 10/1997 | (WO) . |

OTHER PUBLICATIONS

Fan J. et al., "Genetic Mapping: Finding and Analyzing Single–Nucleotide Polymorphisms With High–Density DNA Arrays", *American Journal of Human Genetics*, vol. 61, No. 4, p. 1601 (Oct. 1997).

Wang D.G. et al., "Large–Scale Identification, Mapping and Genotyping of Single–Nucleotide Polymorphisms in the Humand Genome", *Science*, vol. 280, pp. 1077–0/1082, (May 1998).

Sanger F., S. Nicklen and A.R. Coulson (Dec. 1977) "DNA sequencing with chain–terminating inhibitors" vol. 74, No. 12 Proc. Natl. Acad. Sci. USA pp. 5463–5467.

(List continued on next page.)

*Primary Examiner*—Scott W. Houtteman
(74) *Attorney, Agent, or Firm*—Testa Hurwitz & Thibeault LLP

(57) ABSTRACT

Methods are provided for identifying nucleic acids. Methods of the invention are useful for identifying and analyzing nucleic acids, especially variants of single nucleotide polymorphisms, that are indicative of disease or the predisposition for disease.

4 Claims, 3 Drawing Sheets

U.S. PATENT DOCUMENTS

| | | |
|---|---|---|
| 5,380,645 | 1/1995 | Vogelstein . |
| 5,380,647 | 1/1995 | Bahar . |
| 5,382,510 | 1/1995 | Levine et al. . |
| 5,409,586 | 4/1995 | Kamahori et al. . |
| 5,458,761 | 10/1995 | Kamahori et al. . |
| 5,463,782 | 11/1995 | Carlson et al. . |
| 5,466,576 | 11/1995 | Schulz et al. . |
| 5,468,610 | 11/1995 | Polymeropoulos et al. . |
| 5,468,613 | 11/1995 | Erlich et al. . |
| 5,489,508 | 2/1996 | West et al. . |
| 5,492,808 | 2/1996 | de la Chapelle et al. . |
| 5,496,470 | 3/1996 | Lenhart . |
| 5,508,168 | 4/1996 | Kausch et al. . |
| 5,512,441 | 4/1996 | Ronal . |
| 5,514,547 | 5/1996 | Balazs et al. . |
| 5,527,676 | 6/1996 | Vogelstein et al. . |
| 5,532,108 | 7/1996 | Vogelstein . |
| 5,580,729 | 12/1996 | Vogelstein . |
| 5,709,998 | 1/1998 | Kinzler et al. . |

OTHER PUBLICATIONS

Wallace R.B., et al. (1979) "Hybridization of synthetic oligodeoxyribonucleotides to Φχ 174 DNA: the effect of single base pair mismatch" vol. 6, No. 11 *Nucleic Acids Research* pp. 3543–3557.

Coll P., K. Phillips, and F. C. Tenover (Oct. 1989) "Evaluation of a Rapid Method of Extradcting DNA from Stool Samples for Use in Hybridization Assays" vol. 27, No. 10 *Journal of Clinical Microbiology* pp. 2245–2248.

Jessup J. M. and G. E. Gallick (Sep./Oct. 1992) "The Biology of Colorectal Carcinoma" *Current Problems in Cancer* pp. 263–328.

Litia A., L. Liukkonen and H. Siitari (1992) "Simultaneous detection of two cystic fibrosis alleles using dual–label time–resolved fluorometry" 6 *Molecular and Cellular Probes* pp. 505–512.

Young G.P., and B. H. Demediu (1992) "The genetics, epidemiology, and early detection of gastrointestinal cancers" 4 *Current Opinion in Oncology* pp. 728–735.

Hoss M., et al., (Sep. 17, 1992) "Excrement analysis by PCR" *Scientific Correspondence* pp. 199.

Sidransky, et al. (Apr. 3, 1992) "Identification of ras Oncogene Mutations in the Stool of Patients with Curable Colorectal Tumors" vol. 256 *Science* pp. 102–105.

Takeda S., S. Ichii, and Y. Nakamura (1993) "Detection of K–ras Mutation in Sputum by Mutant–Allele–Specific Amplification (MASA)" 2 *Human Mutation* pp.112–117.

Leong P. K., et al. (1993) "Detection of MYCN Gene Amplification and Deletions of Chromosome 1p in Neuroblastoma by In Situ Hybridization Using Routine Histologic Sections" vol. 69, No. 1 *Laboratory Investigations* pp. 43–50.

Thibodeau S.N., G. Bren, D. Schaid (May 7, 1993) "Microsatellite Instability in Cancer of the Proximal Colon" vol. 260 *Science* pp. 816–819.

Naber S. P.(Dec. 1, 1994) "Molecular Pathology—Detection of Neoplasia" 331 *New England Journal of Medicine* pp. 1508–1510.

Cave H., et al. (1994) "Reliability of PCR Directly from Stool Samples: Usefulness of an Internal Standard" vol. 16, No. 5 *Bio Techniques* pp. 809–810.

Caladas C., et al (Jul. 1, 1994) "Detection of K–ras Mutations in the Stool of Patients with Pancreatic Adenocarcinoma and Pancreatic Ductal Hyperplasia" 54 *Cancer Research* pp. 3568–3573.

Charlesworth B., P. Sniegowski and W. Stephan (Sep. 15, 1994) "The evolutionary dynamics of repetitive DNA in eukaryotes" vol. 371 *Nature* pp. 215–220.

Fearon E. R.(1995) "16 Molecular Abnormalities in Colon and Rectal Cancer" *The Molecular Basis of Cancer* pp. 340–357.

Ravelingien N., J. C. Pector & T. Velu (1995) "Contribution of molecular oncology in the detection of colorectal carcinomas" 58 *Acta Gastro–Enterologica Belgica* pp. 270–273.

Duffy M.J. (1995) "Can Molecular Markers Now Be Used for Early Diagnosis of Malignancy?" 41/10 *Clin. Chem.* pp. 1410–1413.

Blum H.E.(1995) "Colorectal Cancer: Future Populatin Screening for Early Colorectal Cancer" vol. 31A *European Journal of Cancer*, pp. 1369–1372.

Ridanpaa M., S. Anttila and K. Husgafvel–Pursiainen (1995) "Detection of Loss of Heterozygosity in the p53 Tumor Suppressor Gene Using a PCR–based Assay" 191 *Path. Res. Pract.* pp. 399–402.

Smith–Ravin J., J. England, I.C. Talbot, W. Bodmer (1995) "Detection of c–Ki–ras mutations in faecal samples from sporadic colorectal cancer patients" 36 *Gut* pp. 81–86.

Orlow I., et al. (Oct. 18, 1995) "Deletion of the p16 and p15 Genes in Human Bladder Tumors" vol. 87, No. 20 *Journal of the National Cancer Institute* pp. 1524–1529.

Hasegawa, Y., et al., (1995) "Detection of K–ras mutations in DNAs isolated from feces of patients with colorectal tumors by mutant–allele–specific amplification (MASA)" 10 *Oncogene* pp. 1441–1445.

Loktionov A. and I. K. O'Neill (1995) "Early detection of cancer–associated gene alterations in DNA isolated from rat feces during intestinal tumor induction with 1,2–dimethylhydrazine" 6 *International Journal of Oncology* pp. 437–445.

Honchel R., K. C. Halling and S. N. Thibodeau (1995) "Genomic instability in neoplasia" vol. 6 *Seminars in Cell Biology* pp. 45–52.

Deuter R., S. Pietsch, S. Hertel and O. Muller (1995) "A method for preparation of fecal DNA suitable for PCR" vol. 23, No. 18 *Nucleic Acids Research* pp. 3800–3801.

Dib C., et al. (Mar. 14, 1996) "A Comprehensive genetic map of the human genome based on 5,264 microsatellites" vol. 380 *Nature* pp. 152–154.

Cunningham C. and M.G. Dunlop (1996) "Molecular genetic basis of colorectal cancer susceptibility" 83 *British Journal of Surgery* pp. 321–329.

Mao L., et al. (Feb. 2, 1996) "Molecular Detection of Primary Bladder Cancer by Microsatellite Analysis" vol. 271 *Science* pp. 659–662.

Villa E., et al. (May 1996) "Identification of Subjects at Risk for Colorectal Carcinoma Through a Test Based on K–ras Determination in the Stool" vol. 110, No. 5 *Gastroenterology* pp. 1346–1353.

Nollau P., C. Moser, G. Weinland, and C. Wagener (1996) "Detection of K–ras Mutations in Stools of Patients with Colorectal Cancer by Mutant–enriched PCR" 66 *Int. J. Cancer* pp. 332–336.

Eguchi S., N. Kohara, K. Komuta, and T. Kanematsu (Arp. 15, 1996) "Mutations of the p53 Gene in the Stool of Patients with Resectable Colorectal Cancer" vol. 77, No. 8 *Cancer Supplement* pp. 1707–1710.

Nollau P., C. Moser, and C. Wagener (May 1996) "Isolation of DNA from Stool and Bodily Fluids for PCR Amplication" vol. 20, No. 5 *Bio Techniques* pp. 784–788.

Rhyu M. S. (Mar. 6, 1996) "Molecular Mechanisms Underlying Hereditary Nonpolyposis Colorectal Carcinoma" vol. 88, No. 5 *Journal of the National Cancer Institute* pp. 240–251.

Gyllensten U. B., Allen M. (1995) "Sequencing of In Vitro Amplified DNA" In *Recombinant DNA Methodology II* (Wu, ed) pp. 565–578.

Myers, R.M., "The Pulses of Subtraction", vol. 259 Science, pp. 942–943 (1993).

Jonsson et al., From Mutation mapping to phenotype cloning: vol. 92 Proc. Natl. Sci. USA, pp. 83–85 (1995).

Watson et al. "Isolation of Differentiality Expressed Sequence Tags from Human Breast Cancer" Advanced in Brief XP 000576043, pp. 4598–4602.

Bos et al., (May 28, 1987) "Prevalence of ras gene mutations in human colorectal cancers" *Nature* vol. 327 pp. 293–297.

Segel, "Biochemical Calculations," John Wiley & Sons, Inc. Ny. pp. 373–376.

Lokionov et al., (Feb., 1998) "Quantitation of DNA from Exfoliated Colonocytes Isolated from Human Stool Surface as a Novel Noninvasive Screening Test for Colorectal Cancer" *Clinical Cancer Research* vol. 4, pp. 337–341.

```
                                          1:              3'ACGCTACGG5'
SEQ ID NO:1    2:    5' ....ATCGGCTTACTGCGATGCC....3'

M

SEQ ID NO:2    3:    3' ....TAGCCGAATGACGCTACGG....5'
               4:         5'ATCGGCTTA3'

1:              3'ACGCTACGG5'
SEQ ID NO:3    2:    5' ....ATCGGCTTATTGCGATGCC....3'

F

SEQ ID NO:4    3:    3' ....TAGCCGAATAACGCTACGG....5'
               4:         5'ATCGGCTTA3'
```

FIG. 1

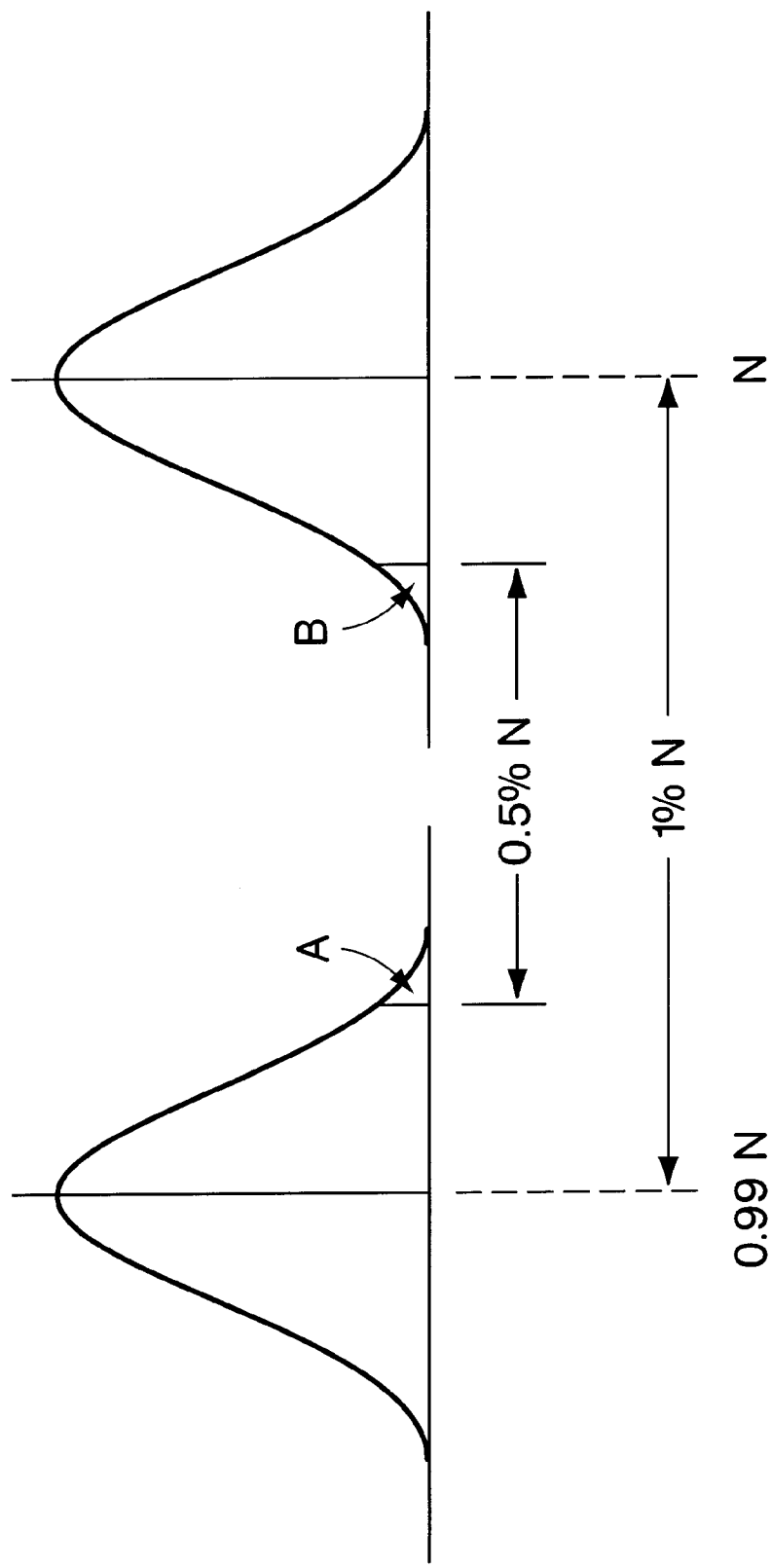

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence:
      hypothetical polymorphism, strand M2
<221> NAME/KEY: allele
<222> LOCATION: (10)
<223> OTHER INFORMATION: Polymorphic site

<400> SEQUENCE: 1
atcggcttac tgcgatgcc                                              19

<210> SEQ ID NO 2

```
<211> LENGTH: 19
<212> TYPE: DNA
<213> ORGANISM: Artificial Sequence
<220> FEATURE:
<223> OTHER INFORMATION: Description of Artificial Sequence:hypothetical
      polymorphism, strand M3
<221> NAME/KEY: allele
<222> LOCATION: (10)
<223> OTHER INFORMATION: Polymorphic site

<400> SEQUENCE: 2
ggcatcgcag taagccgat                                                19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:
      hypothetical polymorphism, strand F2
<221> NAME/KEY: allele
<222> LOCATION: (10)
<223> OTHER INFORMATION: Polymorphic site

<400> SEQUENCE: 3
atcggcttat tgcgatgcc                                                19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:hypothetical
      polymorphism, strand F3
<221> NAME/KEY: allele
<222> LOCATION: (10)
<223> OTHER INFORMATION: Polymorphic site

<400> SEQUENCE: 4
ggcatcgcaa taagccgat                                                19
```

METHODS FOR THE DETECTION OF NUCLEIC ACIDS

This application is a continuation of U.S. patent application, Ser. No. 09/098,180 filed Jun. 16, 1998 now abandoned, which is a continuation-in-part of U.S. Ser. No. 08/876,857, filed Jun. 16, 1997, now U.S. Pat. No. 5,928,870, which is a continuation-in-part of U.S. patent application, Ser. No. 08/700,583 filed Aug. 14, 1996, now U.S. Pat. No. 5,670,325, the disclosure of which is incorporated by reference herein.

FIELD OF THE INVENTION

This invention relates to methods useful for disease diagnosis by detecting changes in nucleic acids, and by detecting the presence of one or more polymorphisms that are indicative of disease.

BACKGROUND OF THE INVENTION

The capacity to diagnose disease is of central concern to human, animal and plant genetic studies, and particularly to inherited disease diagnostics. Genetic disease diagnosis typically is pursued by analyzing variations in DNA sequences that distinguish genomic DNA among members of a population. If such variations alter the lengths of the fragments that are generated by restriction endonuclease cleavage, the variations are referred to as restriction fragment length polymorphisms (RFLPs). Where a heritable trait is linked to a particular RFLP, the presence of the RFLP can be used to predict the likelihood that the trait will be expressed phenotypically. Statistical methods have been developed to permit the multilocus analysis of RFLPs such that complex traits that are dependent upon multiple alleles can be mapped. See S. Lander et al., 83 PROC. NAT'L ACAD. SCI. (U.S.A.) 7353–57 (1986); S. Lander et al., 84 PROC. NAT'L ACAD. SCI. (U.S.A.) 2363–67 (1986); H. Donis-Keller et al., 51 CELL 319–37 (1987); S. Lander et al., 121 GENETICS 185–99 (1989).

In some cases, DNA sequence variations are in regions of the genome that are characterized by short tandem repeats (STRs) that include tandem di- or tri-nucleotide motifs. These tandem repeats are also referred to as variable number tandem repeat (VNTR) polymorphisms. These polymorphisms are used in a large number of genetic mapping studies.

A third class of DNA sequence variations results from single nucleotide polymorphisms (SNPs), also referred to as single base polymorphisms, that exist between individuals of the same species. Such polymorphisms are far more frequent, at least in the human genome, than RFLPs or STRs and VNTRs. In some cases, such polymorphisms comprise mutations that are a determinative characteristic in a genetic disease. Indeed, such mutations may affect a single nucleotide present in a coding sequence sufficiently to cause the disease (e.g., hemophilia, sickle-cell anemia). An example of a single nucleotide polymorphism which predisposes a disease is the three-allelic polymorphism of the apolipoprotein E gene. This polymorphism is due to single base substitutions at two DNA loci on the Apo E gene (Mahley, 240 SCI. 622–30 (1988)). It may explain as much as 10% of the phenotypic variation observed in serum cholesterol levels. More that 90% of patients with type III hyperlipoproteinemia are homozygous for one of the APO E alleles.

In many cases, however, single nucleotide polymorphisms occur in non-coding regions. Single nucleotide polymorphisms in non-coding regions are often still useful as markers for predisposition to disease if a proximal relationship exists between the single nucleotide polymorphic locus and a disease-related gene. A disease-related gene is any gene that, in one or more variant is associated with, or causative of, disease. Despite the central importance of polymorphisms in modern genetics, no practical method has been developed which permits enumerative analysis of disease-associated polymorphic sites.

There is particular interest in molecular mechanisms for the diagnosis of cancer. Cancer is a disease characterized by genomic instability. The acquisition of genomic instability is thought to arise from a coincident disruption of genomic integrity and a loss of cell cycle control mechanisms. Generally, a disruption of genomic integrity is thought merely to increase the probability that a cell will engage in the multistep pathway leading to cancer. However, coupled with a loss of cell cycle control mechanisms, a disruption in genomic integrity may be sufficient to generate a population of genomically unstable neoplastic cells. A common genetic change characteristic of the early stages of transformation is a loss of heterozygosity. Loss of heterozygosity at a number of tumor suppressor genes has been implicated in tumorigenesis. For example, loss of heterozygosity at the P53 tumor suppressor locus has been correlated with various types of cancer. Ridanpaa et al., 191 PATH. RES. PRACT. 399–402 (1995). The loss of the apc and dcc tumor suppressor genes has also been associated with tumor development. Blum, 31A EUROP. J. CANCEr 1369–72 (1995).

Loss of heterozygosity is therefore a potentially useful marker for detecting the early stages of cancer. However, in the early stages of cancer only a small number of cells within a tissue have undergone transformation. Genetic changes characteristic of genomic instability theoretically can serve as markers for the early stages of, for example, colon cancer, and can be detected in DNA isolated from biopsied colonic epithelium and in some cases from transformed cells shed into fecal material. Sidransky et al., 256 SCI., 102–105 (1992).

Detection methods proposed in the art are time-consuming and expensive. Moreover, methods according to the art cannot be used to identify a loss of heterozygosity or microsatellite instability in small subpopulation of cells when the cells exist in a heterogeneous (i.e., clonally impure) sample. For example, in U.S. Pat. No. 5,527,676, it is stated that tissue samples in which a mutation is to be detected should be enriched for tumor cells in order to detect the loss of heterozygosity in a p53 gene.

The present invention provides molecular assays for the detection of nucleic acids, especially nucleic acids that are indicative of disease.

SUMMARY OF THE INVENTION

The present invention provides methods for identifying nucleic acids, particularly single nucleotide loci, and specific single base polymorphic variants, that are diagnostic markers. Methods of the invention are useful for identifying single base loci that are indicative of disease or the predisposition for disease. Alternatively, Methods of the invention are useful for analyzing and identifying variants at known disease-associated loci, such as those available on the Genbank database and other databases.

In general, the invention comprises methods for enumerating (i.e., counting) the number of molecules of one or more nucleic acid variant present in a sample. According to methods of the invention, a disease-associated variant at, for example, a single nucleotide polymorphic locus is determined by enumerating the number of a nucleic acid in a first sample and determining if there is a statistically-significant difference between that number and the number of the same nucleotide in a second sample. Preferably, one sample represents the number of the nucleic acid expected to occur in a sample obtained from a healthy individual, or from a healthy population if pooled samples are used. A statistically-significant difference between the number of a nucleic acid expected to be at a single-base locus in a healthy individual and the number determined to be in a sample obtained from a patient is clinically indicative.

The invention further comprises methods for comparing the number of one or more specific single-base polymorphic variants contained in a sample of pooled genomic DNA obtained from healthy members of an organism population (referred to as the reference number) and an enumerated number of one or more variants contained in a sample of pooled genomic DNA obtained from diseased members of the population (referred to as the target number) to determine whether any difference between the two numbers is statistically significant. The presence of a statistically-significant difference between the reference number and the target number is indicative that the loci (or one or more of the variants) is a diagnostic marker for the disease. An individual patient is screened for the disease by first identifying a variant which is a diagnostic marker for the disease and then screening a sample of the patient's genomic DNA for the presence of the variant. In a patient having a specific variant which is indicative of the presence of a disease-related gene, the severity of the disease can be assessed by determining the number of molecules of the variant present in a standardized DNA sample and applying a statistical relationship to the number. The statistical relationship is determined by correlating the number of a disease-associated polymorphic variant with the number of the variant expected to occur at a given severity level (using, for example, statistical methods described herein).

In a preferred embodiment, enumerative analysis of pooled genomic DNA samples is used to determine the presence or likelihood of disease. Pooled genomic DNA from healthy members of a population and pooled genomic DNA from diseased members of a population are obtained. The number of each variant at a single-nucleotide polymorphic site is determined in each sample. The numbers are analyzed to determine if there is a statistically-significant difference between the variant(s) present in the sample obtained from the healthy population and those present in the sample obtained from the diseased population. A statistically-significant difference indicates that the polymorphic locus is a marker for disease.

Also in a preferred embodiment, methods of the invention are used to identify a nucleic acid (e.g., a polymorphic variant) associated with a disease. Such methods comprise counting the number of a nucleic acid, preferably a single base, in members of a diseased population, and counting numbers of the same nucleic acid in members of a healthy population. A statistically-significant difference in the numbers of the nucleic acid between the two populations is indicative that the interrogated locus is associated with a disease.

Once the polymorphic locus is identifited, either by methods of the invention or by consulting an appropriate database, methods of the invention are useful to determine which variant at the polymorphic locus is associated with a disease. In this case, enumerative methods are used to determine whether there is a statistically-significant difference between the number of a first variant in members of a diseased population, and the number of a second variant at the same locus in members of a healthy population. A statistically-significant difference is indicative that the variant in members of the diseased population is useful as a marker for disease. Using this information, patients are screened for the presence of the variant that is thought to be associated with disease, the presence such a variant being indicative of the presence of disease, or a predisposition for a disease.

Methods of the invention are especially useful for the detection of the presence of, or the predisposition for, colorectal cancer in humans. In a preferred embodiment, methods comprise enumerating a number of a polymorphic variant in a patient, and comparing that number to the number of the variant that would be present in a sample obtained from a healthy member of the population. A statistically-significant difference being indicative of the presence of, or a predisposition for, disease in the patient being tested.

Methods of the invention also take advantage of several important insights which permit, for example, reliable detection of a DNA deletion at a known genomic site characteristic of a known cancer cell type. Methods of the invention are useful for the detection and diagnosis of a genetic abnormality, such as a loss of heterozygosity or, more generally, a mutation, which can be correlated with a disease, such as cancer. In a preferred embodiment, the invention comprises methods for enumerating, in a sample, the number of a nucleic acid indicative of a disease. The invention further comprises comparing the number of molecules with a reference number to determine whether any difference between the two numbers is statistically significant, a statistically significant difference being indicative of a genomic disruption (i.e., loss of heterozygosity or another type of mutation, such as a deletion, addition, substitution or rearrangement).

In a preferred embodiment, enumerative detection of a nucleic acid mutation is accomplished by exposing a nucleic acid sample to first and second radionucleotides. The radionucleotides may be single nucleotides or oligonucleotide probes. The first radionucleotide is capable of hybridizing to a genetic region suspected to be mutated in cancer or precancer cells. The second radionucleotide is capable of hybridizing to a region known not to be mutated in cancer or precancer cells. After washing to remove unhybridized radionucleotides, the number of each of first and second radionucleotides is counted. A statistically-significant difference between the number of first and second radionucleotides is indicative of a mutation in a subpopulation of nucleic acids in the sample.

In preferred methods of the invention, first and second radionucleotides are isolated from other sample components by, for example, gel electrophoresis, chromatography, and mass spectrometry. Also in a preferred embodiment, either or both of the first and second radionucleotides is a chain terminator nucleotide, such as a dideoxy nucleotide. A preferred radionucleotide for use in methods of the invention is selected from the group consisting of $^{32}P$, $^{33}P$, $^{35}S$, $^{3}H$, $^{125}I$, and $^{14}C$. The number of first and second radionucleotides may be determined by counting. Methods of the invention are especially useful for the detection of massive nucleotide deletions, such as those that occur in loss of heterozygosity.

In a preferred embodiment the first and second radiolabeled oligonucleotides are separable from each other. For example, the first and second oligonucleotides are of different sizes and can be separated by gel electrophoresis, chromatography or mass spectrometry. In one embodiment the first and second oligonucleotides are of different lengths. In a preferred embodiment the size difference is imparted by a size marker which is specifically attached to one of the two oligonucleotides. Alternatively a different size marker is attached to each oligonucleotide. After separation, the number of radioactive decay events is measured for each oligonucleotide, and the number of molecules is calculated as described herein.

In a more preferred embodiment, the first and second oligonucleotides are of the same size but are labeled with different radioisotopes selected from, for example, $^{35}S$, $^{32}P$, $^{33}P$, $^{3}H$, $^{125}I$ and $^{14}C$. The first and second oligonucleotides are then distinguished by different characteristic emission spectra. The number of radioactive decay events is measured for each oligonucleotide without separating the two oligonucleotides from each other.

The preferred methods and examples that will now be described are illustrative only and are not intended to be limiting. Other features and advantages of the invention will be apparent from the following detailed description and claims.

DESCRIPTION OF THE DRAWINGS

FIG. 1 depicts differential primer extension as exemplified below.

FIG. 3 is graph showing the probable values of N for a heterogeneous population of cells in which 1% of the cells are mutated.

DETAILED DESCRIPTION OF THE INVENTION

Figure 2A:
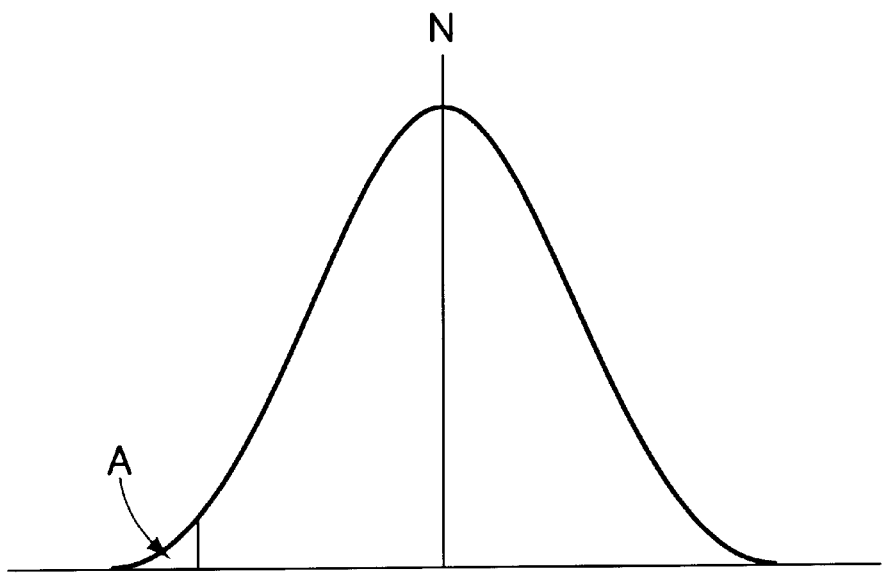
FIGS. 2A and 2B are model Gaussian distributions showing regions of low statistical probability.

The present invention comprises methods for detecting nucleic acids. In preferred embodiments, the invention is directed to the identification, detection, and analysis of informative polymorphisms or polymorphic variants, especially single-nucleotide polymorphisms and variants. According to methods of the invention, enumerative analysis is used to determine whether one or more nucleic acids in a patient sample is a variant that is associated with disease or with the predisposition for disease.

Methods of the invention are especially useful for the detection and diagnosis of a predisposition for a genetic abnormality, such as a loss of heterozygosity, or more generally, a mutation, such as a point mutation, which is indicative of disease. For example, enumerated amounts of a single nucletide variant known to be associated with, for example, cancer, are compared to the amount of the variant known or expected to be present in a separate, non-cancerous sample. A statistically-significant difference between the two numbers is indicative that the variant known to be associated with, for example, cancer is present in the sample, thereby allowing diagnosis of the disease or a predisposition therefor. Accordingly, diagnosis and detection is accomplished by comparing the number of a nucleic acid in a patient sample (e.g., patient tissue or body fluid) with the number of the same nucleic acid that is detected, or would be expected to occur, in a sample from a healthy patient, or pool of healthy patients. A statistically-significant difference between the number of a nucleic acid in a patient sample, and the number expected to be in a healthy patient sample, indicates that the patient sample may contain a nucleic acid variant that is indicative of disease, or a predisposition therefor. A statistically-significant difference can be diagnostic of disease (e.g., when a variant nucleic acid is known to be causative of the disease), diagnostic of a predisposition for a disease (e.g., when a variant nucleic acid is known to be predisposing but not causative), or can indicate the need for further, more invasive diagnostic measures to detect the presence of disease or a predisposing state.

For purposes of exemplification, the following provides details of the use of methods according to the present invention for determining predisposition to certain cancers using variants related to the Multiple Tumor Suppressor gene. Inventive methods are also useful in the diagnosis and analysis of a mutation (and especially a large deletion typical of loss of heterozygosity) in such a tumor suppressor gene. While the following example uses radiolabeled nucleotides and an imager that detects the radioactive decay events, other methods of enumerating may be used, such as hybridization beads used in conjunction with a multi-orfice impedance counter. While exemplified in the following manner, the invention is not so limited and the skilled artisan will appreciate its wide range of applicability upon consideration thereof.

EXAMPLE 1

Human Multiple Tumor Suppressor Gene

The Multiple Tumor Suppressor (MTS) gene is involved in the progression of multiple tumor types, such as melanoma, leukemia, astrocytoma, glioblastoma, lymphoma, glioma, sarcoma, myosarcoma, cholangiocarcinoma, and cancers of the pancreas, breast, brain, prostate, bladder, thyroid, ovary, uterus, testis, kidney, stomach, colon and rectum. Analysis of the MTS gene is useful in predicting predisposition to cancer and the clinical severity and prognosis of patients with MTS-related cancers.

The MTS locus was identified in linkage studies. See Skolnick et al., International Publication No. WO 95/25813. The MTS locus encompasses the MTS1 and MTS2 gene sequences. Mutations in the MTS locus in the germline are indicative of predisposition to melanoma and other cancers. The mutational events of the MTS locus can involve deletions, insertions and point mutations within the coding sequence and the non-coding sequence.

A locus in the MTS gene was identified by Skolnick, et al. as predisposing for melamona. They tested MTS1 and MTS2 genomic DNA from individuals presumed to carry MTS alleles predisposing to melanoma and from individuals presumed not to carry MTS alleles predisposing to melanoma. A single nucleotide polymorphic locus was identified in exon 2 in the MTS1 sequence. The polymorphism results in an amino acid substitution, and was found to segregate with the MTS predisposing allele. The substitutions resulted in either the substitution of a large hydrophobic residue for a small hydrophilic residue, or the substitution of a charged amino acid for a neutral amino acid (specifically, either a substitution of a glycine with a tryptophan, or a valine with a asparagine). This single-nucleotide polymorphic locus is useful as a marker in the methods of the invention.

Using methods of the invention, predisposition to cancers, such as melanoma and the other cancers related to MTS, is ascertained by testing any tissue or body fluid for the presence of disease-associated variants at the MTS locus. The variants to be screened may be alleles on or near the MTS locus, including Exon 2 of the MTS1 sequence. A sample comprising pooled genomic DNA from healthy members of a population presumed not to have the MTS predisposing allele (referred to as the reference sample), and a sample comprising pooled genomic DNA from diseased members of a population presumed to carry the MTS predisposing allele (referred to a the target sample) are prepared. Nucleic acids are sheared or cut into small fragments by, for example, restriction digestion. The size of nucleic acid fragments produced is not critical, subject to the limitations described below. Single-stranded nucleic acid fragments may be prepared using well-known methods. See, e.g., SAMBROOK ET AL., MOLECULAR CLONING, A LABORATORY MANUAL (1989) incorporated by reference herein.

Either portions of a coding strand or its complement may be detected in methods according to the invention. In a preferred embodiment, both first and second strands of an allele are present in a sample during hybridization to an oligonucleotide probe. The sample is exposed to an excess of probe that is complementary to a portion of the first strand, under conditions that promote specific hybridization of the probe to the portion of the first strand. In a most preferred embodiment, the probe is in sufficient excess to bind all the portion of the first strand, and to prevent reannealing of the first strand to the second strand of the allele. Also in a preferred embodiment, the second strand of an allele is removed from a sample prior to hybridization to an oligonucleotide probe that is complementary to a portion of the first strand of the allele. Complement to exons are removed by hybridization to anti-complement oligonucleotide probes (isolation probes) and subsequent removal of duplex formed thereby. Methods for removal of complement strands from a mixture of single-stranded oligonucleotides are known in the art and include techniques such as affinity chromatography. Upon converting double-stranded DNA to single-stranded DNA, sample is passed through an affinity column comprising bound isolation probe that is complementary to the sequence to be isolated away from the sample. Conventional column chromatography is appropriate for isolation of complement. An affinity column packed with sepharose or any other appropriate materials with attached complementary nucleotides may be used to isolate complement DNA in the column, while allowing DNA to be analyzed to pass through the column. See SAMBROOK, supra. As an alternative, isolation beads may be used to exclude complement.

After removal of complement, DNA samples are exposed to radiolabeled nucleotides under conditions which promote specific hybridization. Probes are preferably designed to hybridize specifically (i.e., without mismatches) to a portion of target genomic DNA that contains the polymorphic variant. In a particularly preferred embodiment, four different types of probes are used, each having a different radiolabeled nucleotide in a position to hybridize with the variant nucleotide. The nucleotides in position to hybridize with the variant nucleotide are selected from dATP, dNTP, dCTP, and dGTP, and each is differentially labeled (i.e., with a different isotope or with isotopes of detectably distinct energy levels). Probes are hybridized under conditions that require an exact match of nucleotides in the probe to nucleotides on the target. Upon washing, the only probes that remain bound are those having a labeled nucleotide that is an extact match for the nucleotide at the variant position. If more than one variant is present in a sample, each variant is detected because the nucleotides that have specifically bound to the variant are differentially labeled. The number of molecules of each particular variant is counted by measuring the number of radioactive decay events (e.g., by measuring the total number of counts during a defined interval or by measuring the time it takes to obtain a predetermined number of counts) specifically associated with the particular variant. That number is used to calculate the number of radionucleotides which specifically hybridize with a particular variant in the target sample. The number of each variant present in a healthy sample (preferably pooled healthy samples) is determined in the same manner.

In another preferred embodiment, a single base extension reaction is used in which a sequence-specific probe is hybridized immediately adjacent and usptream to the variant nucleotide to be detected. Each of four differentially-labeled dideoxy nucleotides is then added along with a polymerase under conditions that allow extension of the probe by one base. The number of each dideoxy nucleotides that hybridize at the variant nucleotide position is then determined as described above. Those numbers are compared to numbers obtained from members of a healthy population to determine if there is a statistically-significant difference, the presence of such a difference being indicative of disease or the propensity therefor.

In a preferred embodiment, radioactive decays are used to count the number of a targeted nucleic acid. Preferred isotopes for use in the invention are selected from $^{35}$S, $^{32}$P, $^{33}$P, $^{125}$I, $^{3}$H, and $^{14}$C. In a preferred embodiment, radionucleotides labeled with different isotopes are detected without separating the radionucleotide associated with a first variant from a radionucleotide associated with a second variant. Isotopes useful in the invention have different characteristic emission spectra. The presence of a first isotope does not prevent the measurement of radioactive decay events of a second isotope. In a more preferred embodiment, two different labeled nucleotides of the same molecular weight are used. The two differentially labeled oligonucleotides are electrophoresed on a gel, preferably a denaturing gel, and the gel is exposed to an imager that detects the radioactive decay events of both isotopes. In this embodiment the two isotopes are detected at the same position on the imager, because both oligonucleotides migrate to the same position on the gel. Detection at the same position on the imager reduces variation due to different detection efficiencies at different positions on the imager.

Also in a preferred embodiment, the radionucleotide associated with the particular variant is separated from the radionucleotide associated with another particular variant prior to measuring radioactive decay events. In a preferred embodiment, the separated radionucleotides are labeled with the same isotope. Preferred separation methods comprise conferring different molecular weights to the radionucleotides specifically associated with the particular variant in the target and reference samples.

In a preferred embodiment, first probes comprise a "separation moiety." Such separation moiety is, for example, hapten, biotin, or digoxigenin. The separation moiety in first probes does not interfere with the first probe's ability to hybridize with template or be extended. In an alternative embodiment, the labeled ddNTPs comprise a separation moiety. In yet another alternative embodiment, both the first probes and the labeled ddNTPs comprise a separation moiety. Following the extension reaction, a high molecular weight molecule having affinity for the separation moiety (e g., avidin, streptavidin, or anti-digoxigenin) is added to the reaction mixture under conditions which permit the high molecular weight molecule to bind to the separation moiety. The reaction components are then separated on the basis of molecular weight using techniques known in the art such as gel electrophoresis, chromatography, or mass spectroscopy.

See AUSUBEL ET AL., SHORT PROTOCOLS IN MOLECULAR BIOLOGY (3rd ed., John Wiley & Sons, Inc., 1995); WU, RECOMBINANT DNA METHODOLOGY II (Academic Press, 1995).

Also in a preferred embodiment, the radionucleotide associated with a first variant is separated from the radionucleotide associated with a second variant by differential primer extension, wherein the extension products of a given oligonucleotide primer are of a different length for each of the two variants. In differential primer extension (exemplified in FIG. 1) an oligonucleotide is hybridized such that the 3' nucleotide of the oligonucleotide base pairs with the nucleotide that is immediately 5' of the polymorphic site. The extension reaction is performed in the presence of a radiolabeled terminator nucleotide complementary to the nucleotide at the polymorphic site of the first variant. The reaction may also comprise non-labeled nucleotides complementary to the other 3 nucleotides. Extension of a primer hybridized to a first allele results in a product having only the terminator nucleotide incorporated (exemplified in FIG. 1A, T* is the labeled terminator nucleotide). Extension of a primer hybridized to the second variant results in a product that incorporates several non-labeled nucleotides immediately 5' to the terminator nucleotide (exemplified in FIG. 1B). The number of non-labeled nucleotides that are incorporated is determined by the position, on the template nucleic acid, of the closest 5' nucleotide complementary to the terminator nucleotide. In an alternative embodiment, differential primer extension comprises a labeled oligonucleotide and a non-labeled terminator nucleotide.

Labeled probes are exposed to sample under hybridization conditions. Such conditions are well-known in the art. See, e.g., Wallace et al., 6 NUCLEIC ACIDS RES. 3543–57 (1979), incorporated by reference herein. First and second oligonucleotide probes that are distinctly labeled (i.e. with different radioactive isotopes, fluorescent means, or with beads of different size) are applied to a single aliquot of sample. After exposure of the probes to sample under hybridization conditions, sample is washed to remove any unhybridized probe. Thereafter, hybridized probes are detected separately for each variant. Standards may be used to establish background and to equilibrate results. Also, if differential fluorescent labels are used, the number of probes may be determined by counting differential fluorescent events in a sample that has been diluted sufficiently to enable detection of single fluorescent events in the sample. Duplicate samples may be analyzed in order to confirm the accuracy of results obtained.

If there is a difference between the amount of a particular variant determined in the target sample and the reference sample greater than a 0.5% difference with at least 550,000 events (see below), it is assumed that the particular variant is indicative of a diagnostic disease marker. Statistical significance may be determined by any known method. A preferred method is outlined below.

Enumerative sampling of a nucleotide sequence that is uniformly distributed in a biological sample typically follows a Poisson distribution. For large populations, such as the typical number of genomic polynucleotide segments in a biological sample, the Poisson distribution is similar to a normal (Gaussian) curve with a mean, N, and a standard deviation that may be approximated as the square root of N.

Statistically-significance between numbers of target and reference genes obtained from a biological sample may be determined by any appropriate method. See, e.g., STEEL ET AL., PRINCIPLES & PROC. STATS., A BIOMETRICAL APPROACH (McGraw-Hill, 1980), the disclosure of which is incorporated by reference herein. An exemplary method is to determine, based upon a desired level of specificity (tolerance of false positives) and sensitivity (tolerance of false negatives) and within a selected level of confidence, the difference between numbers of target and reference genes that must be obtained in order to reach a chosen level of statistical significance. A threshold issue in such a determination is the minimum number, N, of genes (for each of target and reference) that must be available in a population in order to allow a determination of statistical significance. The number N will depend upon the assumption of a minimum number of mutant alleles in a sample containing mutant alleles (assumed herein to be at least 1%) and the further assumption that normal samples contain no mutant alleles. It is also assumed that a threshold differences between the numbers of reference and target genes must be at least 0.5% for a diagnosis that there is a mutation present in a subpopulation of cells in the sample. Based upon the foregoing assumptions, it is possible to determine how large N must be so that a detected difference between numbers of mutant and reference alleles of less than 0.5% is truly a negative (i.e. no mutant subpopulation in the sample) result 99.9% of the time.

Figure 2B:
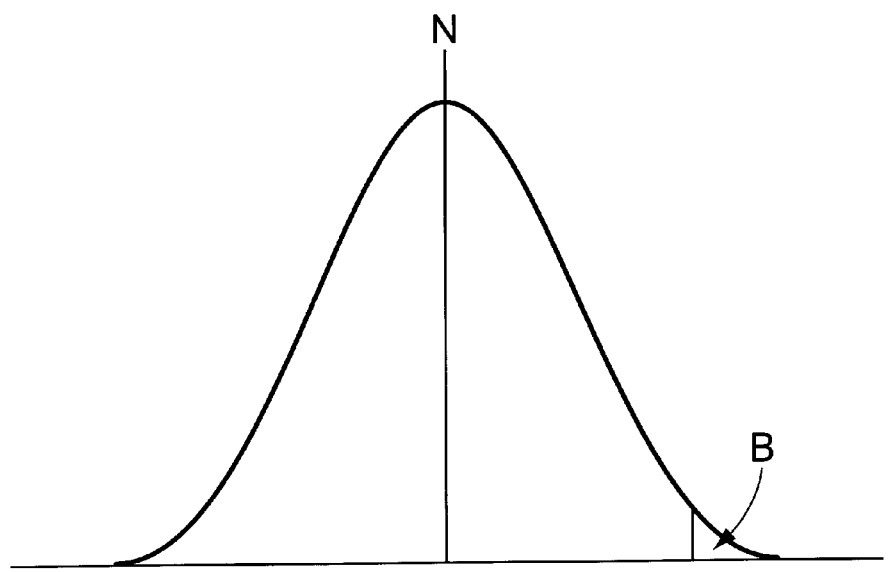

The calculation of N for specificity, then, is based upon the probability of one sample measurement being in the portion of the Gaussian distribution covering the lowest 3.16% of the population (the area marked "A" in FIG. 2A) and the probability that the other sample measurement is in the portion of the Gaussian distribution covering the highest 3.16% of the population (the area marked "B" in FIG. 2B). Since the two sample measurements are independent events, the probability of both events occurring simultaneously in a single sample is approximately 0.001 or 0.1%. Thus, 93.68% of the Gaussian distribution (100%−2×3.16%) lies between the areas marked A and B in FIG. 3. Statistical tables indicate that such area is equivalent to 3.72 standard deviations. Accordingly, 0.5% N is set equal to 3.72 sigma. Since sigma (the standard deviation) is equal to $\sqrt{N}$, the equation may be solved for N as 553,536. This means that if the lower of the two numbers representing reference and target is at least 553,536 and if the patient is truly normal, the difference between the numbers will be less than 0.5% about 99.9% of the time.

To determine the minimum N required for 99% sensitivity a similar analysis is performed. This time, one-tailed Gaussian distribution tables show that 1.28 standard deviations (sigma) from the mean cover 90% of the Gaussian distribution. Moreover, there is a 10% (the square root of 1%) probability of one of the numbers (reference or target) being in either the area marked "A" in FIG. 3 or in the area marked "B" in FIG. 3. If the two population means are a total of 1% different and if there must be a 0.5% difference between the number of target and reference genes, then the distance from either mean to the threshold for statistical significance is equivalent to 0.25% N (See FIG. 3) for 99% sensitivity. As shown in FIG. 3, 0.25% N corresponds to about 40% of one side of the Gaussian distribution. Statistical tables reveal that 40% of the Gaussian distribution corresponds to 1.28 standard deviations from the mean. Therefore, 1.28 sigma is equal to 0.0025N, and N equals 262,144. Thus, for abnormal samples, the difference will exceed 0.5% at least 99% of the time if the lower of the two numbers is at least 262,144. Conversely, an erroneous negative diagnosis will be made only 1% of the time under these conditions.

In order to have both 99.9% specificity (avoidance of false positives) and 99% sensitivity (avoidance of false negatives), a sample with DNA derived from at least 553,536 (or roughly greater than 550,000) cells should be counted. A difference of at least 0.5% between the numbers obtained is significant at a confidence level of 99.0% for sensitivity and a difference of less than 0.5% between the numbers is significant at a confidence level of 99.9% for specificity. As noted above, other standard statistical tests may be used in order to determine statistical significance and the foregoing represents one such test.

Using the above-described methods, a particular variant is identified in Exon 2 of the MTS1 sequence which is indicative of the presence of the MTS predisposing allele. The variant is determined by identifying a statistically-significant difference between a reference number of a particular variant present in a patient sample and a number of the variant present in a separate sample known to be normal (preferably this is the result of pooled samples from normal individuals). An individual patient can be assessed for a predisposition for various cancers by determining the presence or absence of the particular variant in the patient's genomic DNA. The severity of the disease is then assessed by determining a number of molecules of the variant in a standardized sample of the patient's genomic DNA, and applying a predetermined statistical relationship to the number correlating the number with the severity of the disease.

EXAMPLE 2

DETECTION OF THE LOSS OF HETEROZYGOSITY

Methods according to the present invention are useful for the detection of loss of heterozygosity in a heterogeneous cellular sample in which the loss of heterozygosity occurs in only a small subpopulation of cells in the sample. Using traditional detection methods, such a subpopulation would be difficult, if not impossible, to detect especially if the deletion end points are unknown at the time of detection or a clonally-impure cellular population is used. See, e.g., U.S. Pat. No. 5,527,676 (reporting that a clonal population of cells should be used in order to detect a deletion in a p53 gene). Traditional methods for detection of mutations involved in carcinogenesis rely upon the use of a clonally-pure population of cells and such methods are best at detecting mutations that occur at known "hot spots" in oncogenes, such as k-ras. See, Sidransky, supra.

Methods of the present invention are useful for detecting loss of heterozygosity in a small number of cells in an impure cellular population because such methods do not rely upon knowing the precise deletion end-points and such methods are not affected by the presence in the sample of heterogeneous DNA. For example, in loss of heterozygosity, deletions occur over large portions of the genome and entire chromosome arms may be missing. Methods of the invention comprise counting a number of molecules of a target nucleic acid suspected of being deleted and comparing it to a reference number. In a preferred embodiment the reference number is the number of molecules of a nucleic acid suspected of not being deleted in the same sample. All that one needs to know is at least a portion of the sequence of a target nucleic acid suspected of being deleted and at least a portion of the sequence of a reference nucleic acid suspected of not being deleted. Methods of the invention, while amenable to multiple mutation detection, do not require multiple mutation detection in order to detect indicia of cancer in a heterogeneous sample.

Accordingly, methods of the present invention are useful for the detection of loss of heterozygosity in a subpopulation of cells or debris therefrom in a sample. Loss of heterozygosity generally occurs as a deletion of at least one wild-type allelic sequence in a subpopulation of cells. In the case of a tumor suppressor gene, the deletion typically takes the form of a massive deletion characteristic of loss of heterozygosity. Often, as in the case of certain forms of cancer, disease-causing deletions initially occur in a single cell which then produces a small subpopulation of mutant cells. By the time clinical manifestations of the mutation are detected, the disease may have progressed to an incurable stage. Methods of the invention allow detection of a deletion when it exists as only a small percentage of the total cells or cellular debris in a sample.

Methods of the invention comprise a comparison of the number of molecules of two nucleic acids that are expected to be present in the sample in equal numbers in normal (non-mutated) cells. In a preferred embodiment, the comparison is between (1) an amount of a genomic polynucleotide segment that is known or suspected not to be mutated in cells of the sample (the "reference") and (2) an amount of a wild-type (non-mutated) genomic polynucleotide segment suspected of being mutated in a subpopulation of cells in the sample (the "target"). A statistically-significant difference between the amounts of the two genomic polynucleotide segments indicates that a mutation has occurred.

In a preferred embodiment, the reference and target nucleic acids are alleles of the same genetic locus. Alleles are useful in methods of the invention if there is a sequence difference which distinguishes one allele from the other. In a preferred embodiment, the genetic locus is on or near a tumor suppressor gene. Loss of heterozygosity can result in loss of either allele, therefore either allele can serve as the reference allele. The important information is the presence or absence of a statistically significant difference between the number of molecules of each allele in the sample. Also in a preferred embodiment, the reference and target nucleic acids are different genetic loci, for example different genes. In a preferred embodiment, the reference nucleic acid comprises both alleles of a reference genetic locus and the target nucleic acid comprises both alleles of a target genetic locus, for example a tumor suppressor gene. Specifically, in the case of a deletion in a tumor suppressor gene, the detected amount of the reference gene is significantly greater than the detected amount of the target gene. If a target sequence is amplified, as in the case of certain oncogene mutations, the detected amount of target is greater than the detected amount of the reference gene by a statistically-significant margin.

Methods according to the art generally require the use of numerous probes, usually in the form of PCR primers and/or hybridization probes, in order to detect a deletion or a point mutation. However, because methods of the present invention involve enumerative detection of nucleotide sequences and enumerative comparisons between sequences that are known to be stable and those that are suspected of being unstable, only a few probes must be used in order to accurately assess cancer risk. In fact, a single set (pair) of probes is all that is necessary to detect a single large deletion. The risk of cancer is indicated by the presence of a mutation in a genetic region known or suspected to be involved in oncogenesis. Patients who are identified as being at risk based upon tests conducted according to methods of the invention are then directed to other, typically invasive, procedures for confirmation and/or treatment of the disease.

Based upon the foregoing explanation, the skilled artisan appreciates that methods of the invention are useful to detect mutations in a subpopulation of a polynucleotides in any biological sample. For example, methods disclosed herein may be used to detect allelic loss (the loss of heterozygosity)

associated with diseases such as cancer. Additionally, methods of the invention may be used to detect a deletion or a base substitution mutation causative of a metabolic error, such as complete or partial loss of enzyme activity. For purposes of exemplification, the following provides details of the use of methods according to the present invention in colon cancer detection. Inventive methods are especially useful in the early detection of a mutation (and especially a large deletion typical of loss of heterozygosity) in a tumor suppressor gene. Accordingly, while exemplified in the following manner, the invention is not so limited and the skilled artisan will appreciate its wide range of applicability upon consideration thereof.

Methods according to the invention preferably comprise comparing a number of a target polynucleotide known or suspected to be mutated to a number of a reference polynucleotide known or suspected not to be mutated. In addition to the alternative embodiments using either alleles or genetic loci as reference and target nucleic acids, the invention comprises a comparison of a microsatellite repeat region in a normal allele with the corresponding microsatellite region in an allele known or suspected to be mutated. Exemplary detection means of the invention comprise determining whether a difference exists between the number of counts of each nucleic acid being measured. The presence of a statistically-significant difference is indicative that a mutation has occurred in one of the nucleic acids being measured.

A. Preparation of a Stool Sample

A sample prepared from stool voided by a patient should comprise at least a cross-section of the voided stool. As noted above, stool is not homogenous with respect to sloughed cells. As stool passes through the colon, it absorbs sloughed cells from regions of the colonic epithelium with which it makes contacts. Thus, sloughed cells from a polyp are absorbed on only one surface of the forming stool (except near the cecum where stool is still liquid and is homogenized by Intestinal Peristalsis). Taking a representative sample of stool (i.e., at least a cross-section) and homogenizing it ensures that sloughed cells from all epithelial surfaces of the colon will be present for analysis in the processed stool sample. Stool is voided into a receptacle that is preferably small enough to be transported to a testing facility. The receptacle may be fitted to a conventional toilet such that the receptacle accepts stool voided in a conventional manner. The receptacle may comprise a mesh or a screen of sufficient size and placement such that stool is retained while urine is allowed to pass through the mesh or screen and into the toilet. The receptacle may additionally comprise means for homogenizing voided stool. Moreover, the receptacle may comprise means for introducing homogenization buffer or one or more preservatives, such as alcohol or a high salt concentration solution, in order to neutralize bacteria present in the stool sample and to inhibit degradation of DNA.

The receptacle, whether adapted to fit a toilet or simply adapted for receiving the voided stool sample, preferably has sealing means sufficient to contain the voided stool sample and any solution added thereto and to prevent the emanation of odors. The receptacle may have a support frame which is placed directly over a toilet bowl. The support frame has attached thereto an articulating cover which may be placed in a raised position, for depositing of sample or a closed position (not shown) for sealing voided stool within the receptacle. The support frame additionally has a central opening traversing from a top surface through to a bottom surface of the support frame. The bottom surface directly communicates with a top surface of the toilet. Extending from the bottom surface of the support frame and encompassing the entire circumference of the central opening is a means for capturing voided stool. The means for capturing voided stool may be fixedly attached to the support frame or may be removably attached for removal subsequent to deposition of stool.

Once obtained, the stool sample is homogenized in an appropriate buffer, such as phosphate buffered saline or a chaotropic salt solution. Homogenization means and materials for homogenization are generally known in the art. See, e.g., U.S. Pat. No. 4,101,279. Thus, particular homogenization methods may be selected by the skilled artisan. Methods for further processing and analysis of a biological sample, such as a stool sample are presented below.

B. Methods for Detection of Colon Cancer or Precancer

For exemplification, methods of the invention are used to detect a deletion or other mutation in or near the p53 tumor suppressor gene in cells obtained from a representative stool sample. The p53 gene is a good choice because the loss of heterozygosity in p53 is often associated with colorectal cancer. An mRNA sequence corresponding to the DNA coding region for p53 is reported as GenBank Accession No. M92424. The skilled artisan understands that methods described herein may be used to detect mutations in any gene and that detection of a p53 deletion is exemplary of such methods. In the detection of loss of heterozygosity, it is not necessary to target any particular gene due to the massive deletions associated with this event. Accordingly, an LOH-type deletion involving, for example, p53 may be detected by probing a region outside, but near, p53 because that region is also likely to be deleted. At least a cross-section of a voided stool sample is obtained and prepared as described immediately above. DNA or RNA may optionally be isolated from the sample according to methods known in the art. See, Smith-Ravin et al., 36 GUT, 81–86 (1995), incorporated by reference herein. Methods of the invention may also comprise the step of amplifying DNA or RNA sequences using the polymerase chain reaction. However, methods of the invention may be performed on unprocessed stool.

Nucleic acids may be sheared or cut into small fragments by, for example, restriction digestion. The size of nucleic acid fragments produced is not critical, subject to the limitations described below. A target nucleic acid that is suspected of being mutated (p53 in this example) and a reference nucleic acid are chosen. The target and reference nucleic acids may be alleles on or near the p53 gene. Alternatively, the target nucleic acid comprises both alleles on or near the p53 gene and the reference nucleic acid comprises both alleles on or near a genetic locus suspected not to be deleted. Single-stranded nucleic acid fragments may be prepared using well-known methods. See, e.g., SAMBROOK ET AL., MOLECULAR CLONING, LABORATORY MANUAL (1989) incorporated by reference herein.

Either portions of a coding strand or its complement may be detected in methods according to the invention. In a preferred embodiment, both first and second strands of an allele are present in a sample during hybridization to an oligonucleotide probe. The sample is exposed to an excess of probe that is complementary to a portion of the first strand, under conditions to promote specific hybridization of the probe to the portion of the first strand. In a most preferred embodiment, the probe is in sufficient excess to bind all the portion of the first strand, and to prevent reannealing of the first strand to the second strand of the allele. Also in a preferred embodiment, the second strand of an allele is removed from a sample prior to hybridization to an oligonucleotide probe that is complementary to a portion of the first strand of the allele. For exemplification, detection of the coding strand of p53 and reference allele are described. Complement to both p53 and reference allele are removed by hybridization to anti-complement oligonucleotide probes (isolation probes) and subsequent removal of duplex formed thereby. Methods for removal of complement strands from a mixture of single-stranded oligonucleotides are known in the art and include techniques such as affinity chromatography. Upon converting double-stranded DNA to single-stranded DNA, sample is passed through an affinity column comprising bound isolation probe that is complementary to the sequence to be isolated away from the sample. Conventional column chromatography is appropriate for isolation of complement. An affinity column packed with sepharose or any other appropriate materials with attached complementary nucleotides may be used to isolate complement DNA in the column, while allowing DNA to be analyzed to pass through the column. See Sambrook, supra. As an alternative, isolation beads may be used to exclude complement as discussed in detail below.

After removal of complement, the target and reference nucleic acids are exposed to radio-labeled nucleotides under conditions which promote specific association of the radio-labeled nucleotides with the target and reference nucleic acids in a sample. In order to count the number of molecules of the target and reference nucleic acids, the radionucleotides associated with the target nucleic acid must be distinguished from the radionucleotides associated with the reference nucleic acid. In addition, the radionucleotides that are specifically associated with either target or reference nucleic acid must be distinguished from radionucleotides that are not associated with either nucleic acid. The number of molecules of target nucleic acid is counted by measuring a number X of radioactive decay events (e.g. by measuring the total number of counts during a defined interval or by measuring the time it takes to obtain a predetermined number of counts) specifically associated with the target nucleic acid. The number X is used to calculate the number X1 of radionucleotides which are specifically associated with the target nucleic acid. The number X1 is used to calculate the number X2 of target nucleic acid molecules, knowing the ratio of radionucleotide molecules to target nucleic acid molecules in the assay.

According to methods of the invention, it is important to count the number of molecules in order to provide a statistical analysis of the likelihood of loss of heterozygosity. Comparison of the numbers of radioactive decays without knowing the numbers of molecules associated with the radioactive decays does not provide statistical data on the significance of any observed difference.

In a preferred embodiment, a radionucleotide is incorporated into a specific oligonucleotide prior to exposure to the sample. In a most preferred embodiment, a radiolabeled oligonucleotide is used which comprises a single radionucleotide molecule per oligonucleotide molecule. A radiolabeled oligonucleotide is designed to hybridize specifically to a target nucleic acid. In one embodiment the target nucleic acid is a specific allele of a polymorphic genetic locus, and the oligonucleotide is designed to be complementary to the allele at the site of polymorphism. One skilled in the art can perform hybridizations under conditions which promote specific hybridization of the oligonucleotide to the allele, without cross hybridizing to other alleles. Similarly, radiolabeled oligonucleotides are designed to specifically hybridize with the reference nucleic acid.

Also in a preferred embodiment, a radionucleotide is specifically incorporated into an oligonucleotide by primer extension, after exposing the oligonucleotide to the sample under conditions to promote specific hybridization of the oligonucleotide with the target nucleic acid. In a preferred embodiment the oligonucleotide is unlabeled, and the radionucleotide is a radiolabeled chain terminating nucleotide (e.g. a dideoxynucleotide). In a most preferred embodiment, the radionucleotide is the chain terminating nucleotide complementary to the nucleotide immediately 5' to the nucleotide that base pairs to the 3' nucleotide of the oligonucleotide when it is specifically hybridized to the target nucleic acid. In the embodiment where the target nucleic acid is an allele of a polymorphic genetic locus, the oligonucleotide is preferably designed such that the 3' nucleotide of the oligonucleotide base pairs with the nucleotide immediately 3' to the polymorphic residue. In a preferred embodiment, a radiolabeled terminating nucleotide that is complementary to the residue at the polymorphic site is incorporated on the 3' end of the specifically hybridized oligonucleotide by a primer extension reaction. Similarly, in a preferred embodiment, a radionucleotide is specifically associated with a reference nucleic acid by primer extension. Other methods for specifically associating a radioactive isotope with a target or reference nucleic acid (for example a radiolabeled sequence specific DNA binding protein) are also useful for the methods of the invention.

In a preferred embodiment, prior to counting the radioactive decay events, the radionucleotides specifically associated with target and reference nucleic acids are separated from the radionucleotides that are not specifically associated with either nucleic acid. Separation is performed as described herein, or using techniques known in the art. Other separation techniques are also useful for practice of the invention. Methods of the invention also comprise distinguishing the radio-label specifically associated with a target nucleic acid from the radio-label specifically associated with a reference nucleic acid. In a preferred embodiment the isotope associated with the target is different from the isotope associated with the receptor. Different isotopes useful to radio-label nucleotides include $^{35}S$, $^{32}P$, $^{33}P$, $^{125}I$, $^{3}H$, and $^{14}C$. In one embodiment, an oligonucleotide complementary to a target nucleic acid is labeled with a different isotope from an oligonucleotide complementary to a reference nucleic acid. In another embodiment, the chain terminating nucleotide associated with the target nucleic acid is different from the chain terminating nucleotide associated with the reference nucleic acid, and the two chain terminating nucleotides are labeled with different isotopes.

In a preferred embodiment, radionucleotides labeled with different isotopes are detected without separating the radionucleotide associated with the target nucleic acid from the radionucleotide associated with the reference nucleic acid. The different isotopes useful to the invention have different characteristic emission spectra. The presence of a first isotope does not prevent the measurement of radioactive decay events of a second isotope. In a more preferred embodiment, the labeled oligonucleotide associated with the target nucleic acid is the same size as the labeled oligonucleotide associated with the reference nucleic acid (the labeled oligonucleotides can be labeled prior to hybridization or by primer extension). The two differentially labeled oligonucleotides are electrophoresed on a gel, preferably a denaturing gel, and the gel is exposed to an imager that detects the radioactive decay events of both isotopes. In this embodiment the two isotopes are detected at the same position on the imager, because both oligonucleotides migrate to the same position on the gel. Detection at the same position on the imager reduces variation due to different detection efficiencies at different positions on the imager.

Also in a preferred embodiment, the radionucleotide associated with the target nucleic acid is separated from the radionucleotide associated with the reference nucleic acid prior to measuring radioactive decay events. In a preferred embodiment the separated radionucleotides are labeled with the same isotope.

Preferred separation methods comprise conferring different molecular weights to the radionucleotides specifically associated with the target and reference nucleic acids.

In a preferred embodiment, first probes comprise a "separation moiety." Such separation moiety is, for example, hapten, biotin, or digoxigenin. The separation moiety in first probes does not interfere with the first probe's ability to hybridize with template or be extended. In an alternative embodiment, the labeled ddNTPs comprise a separation moiety. In yet another alternative embodiment, both the first probes and the labeled ddNTPs comprise a separation moiety. Following the extension reaction, a high molecular weight molecule having affinity for the separation moiety (e.g., avidin, streptavidin, or anti-digoxigenin) is added to the reaction mixture under conditions which permit the high molecular weight molecule to bind to the separation moiety. The reaction components are then separated on the basis of molecular weight using techniques known in the art such as gel electrophoresis, chromatography, or mass spectroscopy. See, AUSUBEL ET AL., SHORT PROTOCOLS IN MOLECULAR BIOLOGY (3rd ed. John Wiley & Sons, Inc., 1995); WU, RECOMBINANT DNA METHODOLOGY II, (Academic Press, 1995).

Also in a preferred embodiment the radionucleotide associated with a first allele of a polymorphic genetic locus is separated from the radionucleotide associated with a second allele of the polymorphic locus by differential primer extension, wherein the extension products of a given oligonucleotide primer are of a different length for each of the two alleles. In differential primer extension (exemplified in FIG. 1) an oligonucleotide is hybridized such that the 3' nucleotide of the oligonucleotide base pairs with the nucleotide that is immediately 5' of the polymorphic site. The extension reaction is performed in the presence of a radiolabeled terminator nucleotide complementary to the nucleotide at the polymorphic site of the first allele. The reaction also comprises non-labeled nucleotides complementary to the other 3 nucleotides. Extension of a primer hybridized to the first allele results in a product having only the terminator nucleotide incorporated (exemplified in FIG. 1A, T* is the labeled terminator nucleotide). Extension of a primer hybridized to the second allele results in a product that incorporates several non-labeled nucleotides immediately 5' to the terminator nucleotide (exemplified in FIG. 1B). The number of non-labeled nucleotides that are incorporated is determined by the position, on the template nucleic acid, of the closest 5' nucleotide complementary to the terminator nucleotide. In an alternative embodiment, differential primer extension comprises a labeled oligonucleotide and a non-labeled terminator nucleotide.

Labeled probes are exposed to sample under hybridization conditions. Such conditions are well-known in the art. See, e.g., Wallace et al., 6 NUCLEIC ACIDS RES. 3543–57 (1979), incorporated by reference herein. First and Second oligonucleotide probes that are distinctly labeled (i.e. with different radioactive isotopes, fluorescent means, or with beads of different size) are applied to a single aliquot of sample. After exposure of the probes to sample under hybridization conditions, sample is washed to remove any unhybridized probe. Thereafter, hybridized probes are detected separately for p53 hybrids and reference allele hybrids. Standards may be used to establish background and to equilibrate results. Also, if differential fluorescent labels are used, the number of probes may be determined by counting differential fluorescent events in a sample that has been diluted sufficiently to enable detection of single fluorescent events in the sample. Duplicate samples may be analyzed in order to confirm the accuracy of results obtained.

If there is a difference between the amount of p53 detected and the amount of the reference allele detected greater than a 0.5% difference with at least 550,000 events (earlier shown to be the threshold of significance), it may be assumed that a mutation has occurred in the region involving p53 and the patient is at risk for developing or has developed colon cancer. Statistical significance may be determined by any known method. A preferred method is outlined above.

The determination of a p53 mutation allows a clinician to recommend further treatment, such as endoscopy procedures, in order to further diagnose and, if necessary, treat the patient's condition. The following examples illustrate methods of the invention that allow direct quantification of hybridization events.

What is claimed is:

1. A method for determining the severity of a disease of a patient, the method comprising the steps of:
   (a) determining a number of a genomic polymorphic variant, the presence of which is a diagnostic disease marker, at a single base polymorphic locus in a genomic DNA sample obtained from the patient;
   (b) applying to said number a predetermined statistical relationship, said statistical relationship correlating numbers of said genomic polymorphic variants in a sample comprising pooled genomic DNA obtained from members of a population of having said disease, with the clinical severity of said disease; and
   (c) determining the clinical severity of said disease of the patient.

2. A method for identifying a single base polymorphic locus as a marker for a disease treatment, the method comprising the steps of:
   (a) obtaining a first sample comprising pooled genomic DNA from members of an organism population, said members having undergone a successful treatment of said disease;
   (b) obtaining a second sample comprising pooled genomic DNA from members of said population, said members having undergone an unsuccessful treatment of said disease;
   (c) determining whether a statistically-significant difference exists between an enumerated number of a single base polymorphic variant at a single base polymorphic locus in said first sample and an enumerated number of a single base polymorphic variant at said locus in said second sample,
   said difference being indicative that said locus is a marker for a disease treatment.

3. A method for identifying a combination of nucleic acid variants, the presence of said combination being indicative of a marker for a disease treatment, said combination comprising one or more of said variants, the method comprising the steps of:
   (a) determining a first set of numbers, said first set comprising an enumerated number for each of said one or more of said variants in a sample obtained from members of a population having undergone a successful treatment for a disease;
   (b) determining a second set of numbers, said second set comprising an enumerated number for each of said one or more of said variants in a sample obtained from members of said population having undergone an unsuccessful treatment for said disease; and
   (c) determining whether there is a statistically-significant difference between said first set of numbers and said second set of numbers, the presence of said difference being indicative that said combination of nucleic acid variants is indicative of a disease treatment.

4. A method for identifying a single base polymorphic locus as a marker for toxicity of a pharmaceutical compound, the method comprising the steps of:

(a) obtaining a first sample comprising pooled genomic DNA from members of an organism population, said members having been administered a pharmaceutical compound without displaying an indication of a toxic effect;

(b) obtaining a second sample comprising pooled genomic DNA from members of said population, said members having been administered a pharmaceutical compound and having displayed an indication of a toxic effect;

(c) determining whether a statistically-significant difference exists between an enumerated number of a single base polymorphic variant at a single base polymorphic locus in said first sample and an enumerated number of a single base polymorphic variant at said locus in said second sample, said difference being indicative that said locus is a marker for toxicity of a pharmaceutical compound.

* * * * *